United States Patent
Bogue et al.

(10) Patent No.: US 8,650,931 B1
(45) Date of Patent: Feb. 18, 2014

(54) SELF-SEALING FUEL TANK TEST FIXTURES

(75) Inventors: Bradley Wayne Bogue, Collinsville, IL (US); Charles Edward Hagar, Manchester, MO (US)

(73) Assignee: The Boeing Company, Chicago, IL (US)

( * ) Notice: Subject to any disclaimer, the term of this patent is extended or adjusted under 35 U.S.C. 154(b) by 402 days.

(21) Appl. No.: 13/105,530

(22) Filed: May 11, 2011

(51) Int. Cl.
*G01M 7/00* (2006.01)
*G01N 3/00* (2006.01)
*G01N 33/00* (2006.01)
*G01P 15/00* (2006.01)

(52) U.S. Cl.
USPC ............. 73/12.11; 73/12.01; 220/560.02; 220/560.03

(58) Field of Classification Search
USPC .............. 73/12.05, 12.11, 37, 38, 49.8; 220/560.02, 560.03; 137/15.11
See application file for complete search history.

(56) References Cited

U.S. PATENT DOCUMENTS

| 3,591,050 A | * | 7/1971 | Kupersmith et al. | 222/23 |
| 4,886,225 A | * | 12/1989 | Bates | 244/135 R |
| 5,036,696 A | * | 8/1991 | Ahrens et al. | 73/12.11 |

OTHER PUBLICATIONS

"Detail Specification Tanks, Fuel, Aircraft, Self-Sealing," MIL-DTL-5578D; Aug. 8, 2008.
"Detail Specification for the Tank, Fuel, Crash-Resistant, Ballistic-Tolerant, Aircraft" MIL-DTL-27422C; Jan. 14, 2002.

* cited by examiner

*Primary Examiner* — Lisa Caputo
*Assistant Examiner* — Roger Hernandez-Prewitt
(74) *Attorney, Agent, or Firm* — Hope Baldauff, LLC

(57) ABSTRACT

Concepts and technologies are disclosed herein for providing and using self-sealing fuel tank test fixtures. According to some embodiments disclosed herein, a self-sealing fuel tank test fixture includes a fuel cube configured for storing fuel. The fuel cube includes a front side configured to support a test sample for the test. The self-sealing fuel tank test fixtures also can include a knife valve selectively configurable from a first position in which the fuel in the fuel cube is separated from the front side and a second position in which the fuel in the fuel cube is allowed to contact the test sample.

20 Claims, 6 Drawing Sheets

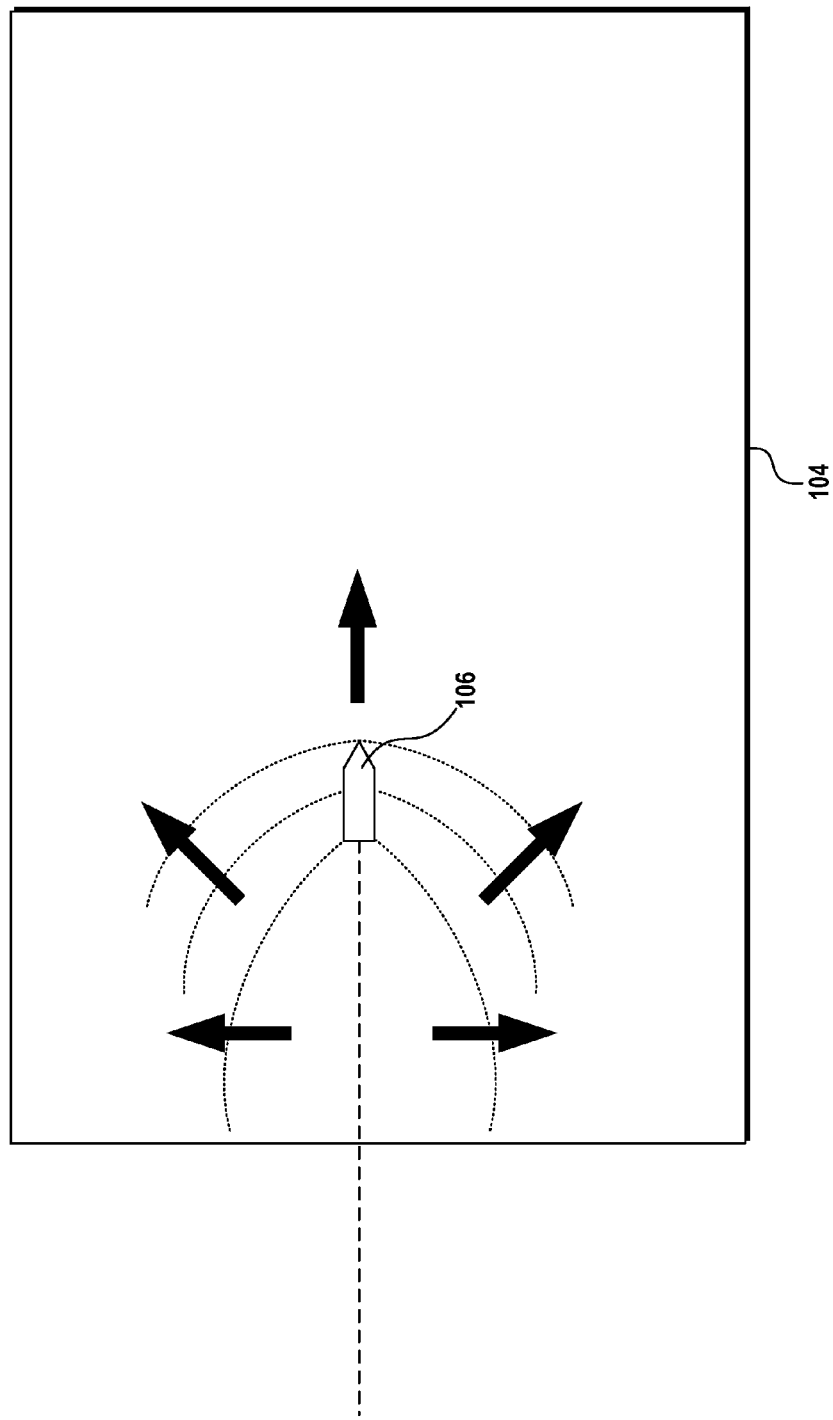

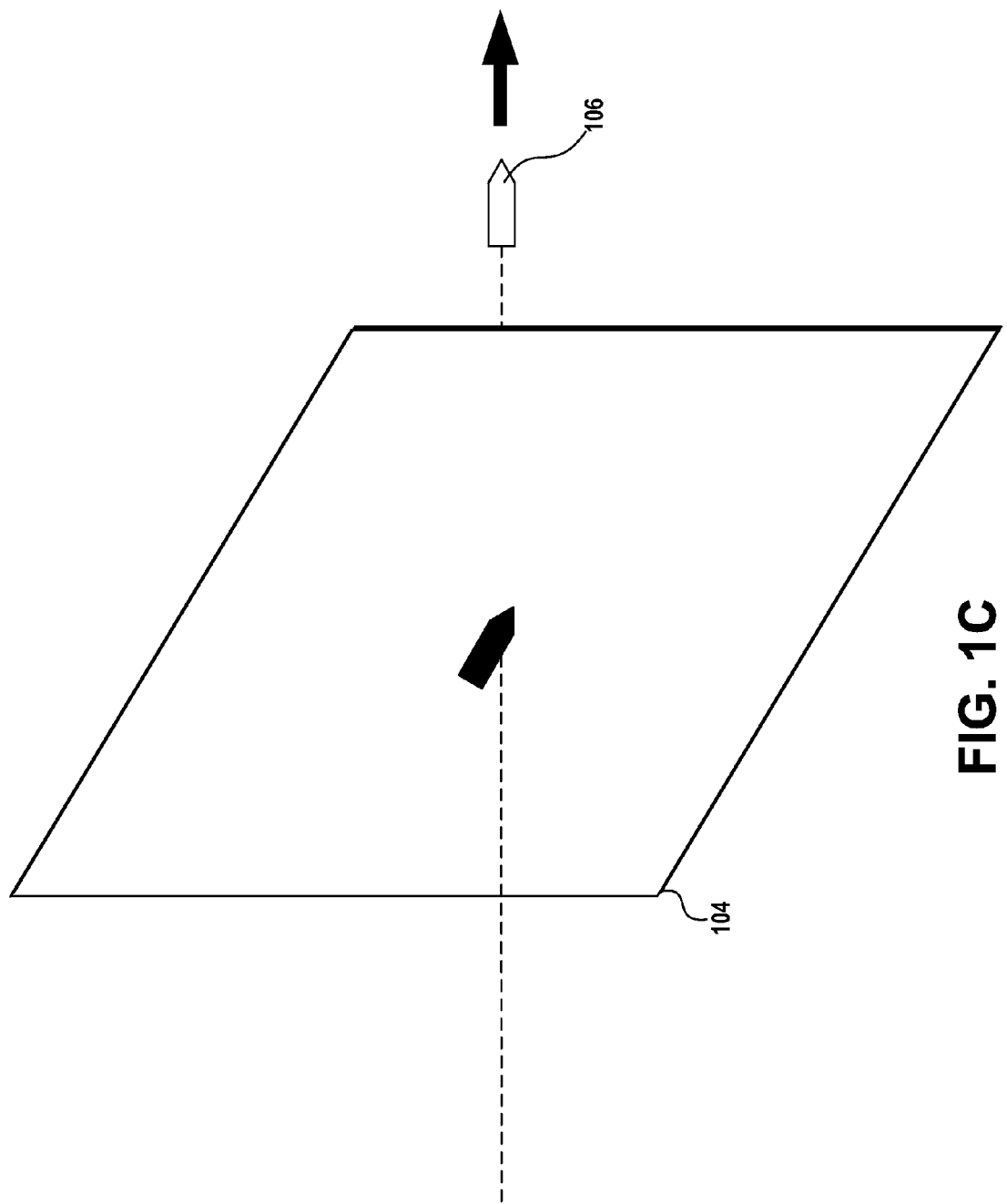

SELF-SEALING FUEL TANK TEST FIXTURES

TECHNICAL FIELD

The present disclosure relates generally to test fixtures and, more particularly, to self-sealing fuel tank test fixtures.

BACKGROUND

Self-sealing materials are sometimes used in fuel tanks to reduce fuel loss and/or the risk of explosion resulting from punctures of the fuel tanks due to gunfire and/or other causes. In some examples of self-sealing fuel tanks, fuel and/or fuel additives in the fuel tank and self-sealing materials used in the fuel tank react with one another to create a seal. Thus, if fuel begins leaking out of the fuel tank, a reaction between the fuel and/or fuel additives and the self-sealing materials can cause swelling that operates to seal holes in the fuel tank.

New materials and fuel additives are developed frequently. As such, fuel tanks, fuels, fuel additives, and various other aspects of self-sealing fuel tanks are often subjected to testing to evaluate expected performance of the self-sealing fuel tanks. As such, the self-sealing materials can be evaluated for combat or other situations in which the fuel tanks may be punctured or otherwise leak.

Test fixtures exist for subjecting self-sealing materials to gunfire testing. Some example test fixtures include an aluminum housing that is sometimes secured to a steel frame. A fuel tank formed from self-sealing material is disposed within the aluminum housing. The test fixture is tested with gunfire or other penetration methods and performance of the self-sealing material thus can be evaluated.

In conventional test fixtures, however, gauging how much fuel is lost during the test and/or determining how long the wound takes to heal are difficult to gauge. Also, the conventional test fixtures can cause and/or exacerbate hydrodynamic ram and projectile coring, two phenomena that can prevent sealing of the self-sealing material and as such, failure of the fuel tank testing. Furthermore, it can be difficult to access the test sample due to the construction and/or materials of the housing.

It is with respect to these and other considerations that the disclosure made herein is presented.

SUMMARY

It should be appreciated that this Summary is provided to introduce a selection of concepts in a simplified form that are further described below in the Detailed Description. This Summary is not intended to be used to limit the scope of the claimed subject matter.

According to one aspect of the embodiments disclosed herein, a self-sealing fuel tank test fixture includes a fuel cube configured for storing fuel. The fuel cube can have a front side that can be configured to support a test sample for a puncture test. The self-sealing fuel tank test fixture also can include a valve that is positioned near the front side of the fuel cube. The valve can be selectively configurable between two positions. In the first position, the fuel in the fuel cube is separated from the front side, and in the second position, the fuel in the fuel cube is allowed to contact the test sample.

According to another aspect of the embodiments disclosed herein, a system for testing a test sample of self-sealing material is provided. The system includes a device for firing a projectile at the test sample and a self-sealing fuel tank test fixture. The self-sealing fuel tank test fixture can be configured to hold the test sample in a position at a front side of the self-sealing fuel tank test fixture for the testing. The front side can correspond to a side of the self-sealing fuel tank test fixture that faces a device that fires a projectile at the test sample. The self-sealing fuel tank test fixture can include a fuel cube configured to store fuel and a knife valve disposed proximate to the fuel cube. The knife valve can be selectively configurable from a first position to a second position. In the first position, fuel in the fuel cube can be separated from the test sample. At the second position, the fuel in the fuel cube can be allowed to contact the test sample.

According to yet another aspect of the embodiments disclosed herein, a method for using a self-sealing fuel tank test fixture to test a self-sealing test sample is provided. The method includes locating the test sample at a front side of the self-sealing fuel tank test fixture and locating a support material at the front side of the self-sealing fuel tank test fixture. The method also can include opening a valve proximate to the test sample, wherein opening the valve allows fuel in a fuel cube of the self-sealing fuel tank test fixture to contact the test sample. The method also includes, in various embodiments, injecting gas into the fuel and firing a projectile at the test sample.

The features, functions, and advantages discussed herein can be achieved independently in various embodiments of the present invention or may be combined in yet other embodiments, further details of which can be seen with reference to the following description and drawings.

BRIEF DESCRIPTION OF THE DRAWINGS

FIG. 1B is a line diagram schematically illustrating the effects of hydrodynamic ram, according to an illustrative embodiment.

FIG. 1C is a line diagram schematically illustrating the effects of projectile coring, according to an illustrative embodiment.

DETAILED DESCRIPTION

Figure 1A:
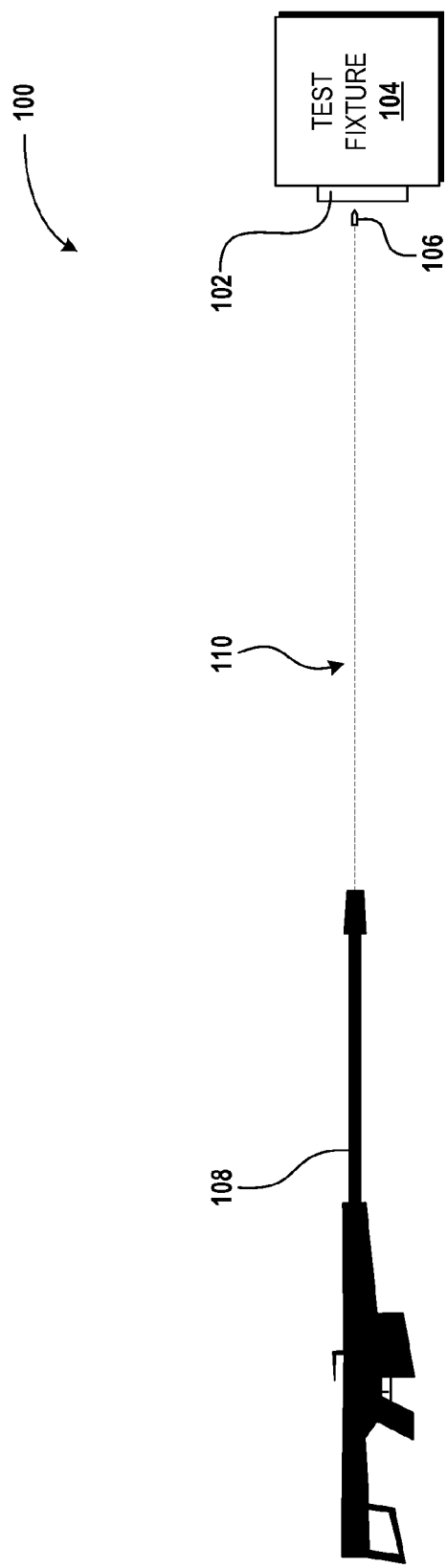
FIG. 1A is a line diagram illustrating a self-sealing fuel tank testing environment, according to an illustrative embodiment.

The following detailed description is directed to self-sealing fuel tank test fixtures. According to the concepts and technologies disclosed herein, a self-sealing test fixture is configured to support a test sample located in front of a fuel cube filled with fuel. The fuel cube includes a top shock impedance area and a low shock impedance area for absorbing shockwaves induced by projectiles fired at the test sample, and a striker and attenuation assembly for stopping the projectile to prevent puncturing of the test fixture. The test fixture also includes structures for introducing nitrogen or other gases into the fuel to further absorb shockwaves induced by the projectiles.

According to some implementations, the test fixture includes a valve for isolating the fuel from a fuel plenum adjacent to the test sample and a face plate that provides quick visual access to the test sample. A drain path can exist between the test sample and a drain basin for catching fuel that leaks through or around the test sample and/or other materials. In various implementations, for example, support materials are disposed in front of a projectile path and the test sample, and the projectile passes through the support materials and the test sample. These and other aspects of the test fixture can reduce or eliminate projectile coring sometimes associated with testing of various structures. These and other advantages and features will become apparent from the description of the various embodiments below.

In the following detailed description, references are made to the accompanying drawings that form a part hereof and that show, by way of illustration, specific embodiments or examples. In referring to the drawings, like numerals represent like elements throughout the several figures.

FIG. 1A illustrates a self-sealing fuel tank testing environment ("test environment") 100, according to an illustrative embodiment. The test environment 100 includes a sample of material ("test sample") 102, which can be attached to, mounted to, and/or otherwise located at a self-sealing fuel tank test fixture ("test fixture") 104. Additional details of the test fixture 104 are illustrated and described below, particularly with reference to FIGS. 2-4.

The test sample 102 is located at the test fixture 104 such that the test sample 102 can be subjected to testing with a projectile 106. The test sample 102 can be formed from any suitable material and/or combination of materials. In some embodiments, the test sample 102 is formed from a self-sealing material that is suitable for use in fuel tanks and/or other structures. Self-sealing materials suitable for use in fuel tanks and other applications are generally known, and therefore are not described in additional detail herein.

The projectile 106 fired at the test sample 102 can be fired from any suitable device. In some embodiments, the projectile 106 is fired from a firearm 108. In other embodiments, the projectile is fired using one or more propellants, springs or other mechanical structures, electromagnetic energy generated by a rail gun or other suitable device, other technologies, combinations thereof, or the like. According to one embodiment, the projectile 106 is a .50 caliber projectile that is fired from the firearm 108. The projectile 106 exits the firearm 108, travels along a projectile path 110, and strikes a target, namely, the test sample 102 and the test fixture 104. It should be understood that this embodiment is illustrative, and should not be construed as being limiting in any way.

In some test scenarios, the projectile 106 is fired such that the projectile 106 tumbles before striking the test sample 102. In some instances, the projectile 106 transfers an increased amount of energy to the test sample 102 when tumbling, relative to an amount of energy transferred to the test sample 102 if the projectile 106 is not tumbling, and therefore can be used to improve results from the testing relative to tests conducted using non-tumbling projectiles 106. According to various implementations, the tumbling induced in the test environment 100, as well as energy otherwise associated with the firing of the projectile 106, can contribute to the occurrence of two phenomena associated with gunfire testing and gunfire damage in general, namely hydrodynamic ram and projectile coring.

Hydrodynamic ram is a phenomenon that can be caused by fluid displacement during gunfire testing of liquid filled structures. Hydrodynamic ram is schematically illustrated in FIG. 1B. In particular, as shown in FIG. 1B, if the projectile 106 enters a structure such as a fixture 104 that is filled or partially filled with a fluid, a shockwave induced by the projectile 106 can transfer energy from the projectile 106 to the fluid, and the shockwave can be transferred from the fluid to the structure containing the fluid. As is generally known, a standard .50 caliber bullet weighs about 750 grains, or about 48.5 grams, and travels at around 2800-3200 feet per second, thereby creating about 2000-3000 foot pounds of energy that can be transferred to a target upon impact. As such, during gunfire or other puncture testing of a fluid-filled target, a tremendous amount of energy can be transferred from a bullet or other projectile 106 to the fluid and/or a structure containing the fluids.

Because many fluids are not compressible or are only minimally compressible, the displacement of the fluid by the projectile 106 can lead to cracking or rupturing of the structure being tested and/or can cause the self-sealing material of the test sample 102 to fail. This effect, referred to herein as "hydrodynamic ram," can interfere with the function of the test sample 102. For example, in the case of self-sealing materials, the hydrodynamic ram can degrade or destroy a seal created by the self-sealing materials and/or destroy the target by rupturing the test sample 102 in a manner that prevents self-sealing. As such, hydrodynamic ram effects can cause test failures and/or damage to structures used for testing or test samples 102 subjected to the testing. As will be explained in more detail below, the test fixture 104 disclosed herein can be used to minimize or eliminate the effects of hydrodynamic ram, thereby improving test results and improving the chances that a test sample 102 will survive testing.

Projectile coring is another effect sometimes encountered during gunfire or other puncture testing. Projectile coring is schematically illustrated in FIG. 1C. In particular, as shown in FIG. 1C, a bullet such as the projectile 106 generally rotates at a high rate of speed due to rifling in a barrel of the firearm 108 or other device used to fire the projectile. Thus, the projectile 106 generally cuts a hole into a target and creates an exit wound. The exit wound is often exhibited by petalling, as is generally known. In some circumstances, the projectile 106 creates an effect similar to a punch or a cookie cutter, wherein the projectile 106, instead of cutting a hole into the target, severs a hole into the target and removes a portion of material from the target. This is shown in FIG. 1C as a dark hole in the structure such as a surface of a fixture 104. As such, the projectile 106 can form a hole that approximates the contours of the projectile 106. This effect is referred to herein as "projectile coring."

Projectile coring can prevent sealing of a self-sealing material. In particular, in the case of a .50 caliber bullet, a core or hole having a diameter of approximately 0.510 inches (the diameter of a .50 caliber bullet) may be formed in the target. A hole having a diameter of 0.510 inches may be too large for the self-sealing material to properly function, and therefore can cause the test to fail. If the projectile 106 is tumbled during testing, the hole can be even larger than 0.510 inches in diameter. In particular, the hole can have a height or width of about 0.510 inches and a length up to the length of the bullet, in this case over two inches. As such, projectile coring during testing of self-sealing fuel tanks and/or self-sealing fuel tank material can make evaluation of the materials being tested difficult if not impossible.

According to various embodiments of the concepts and technologies disclosed herein, the test fixture 104 includes various structures that allow easy evaluation of the test sample 102. Furthermore, the various embodiments of the concepts and technologies disclosed herein also can be used to reduce and/or eliminate hydrodynamic ram and/or projectile coring as described herein. These and other features of the concepts and technologies disclosed herein will be discussed in more detail below with reference to FIGS. 2-4.

Figure 2:
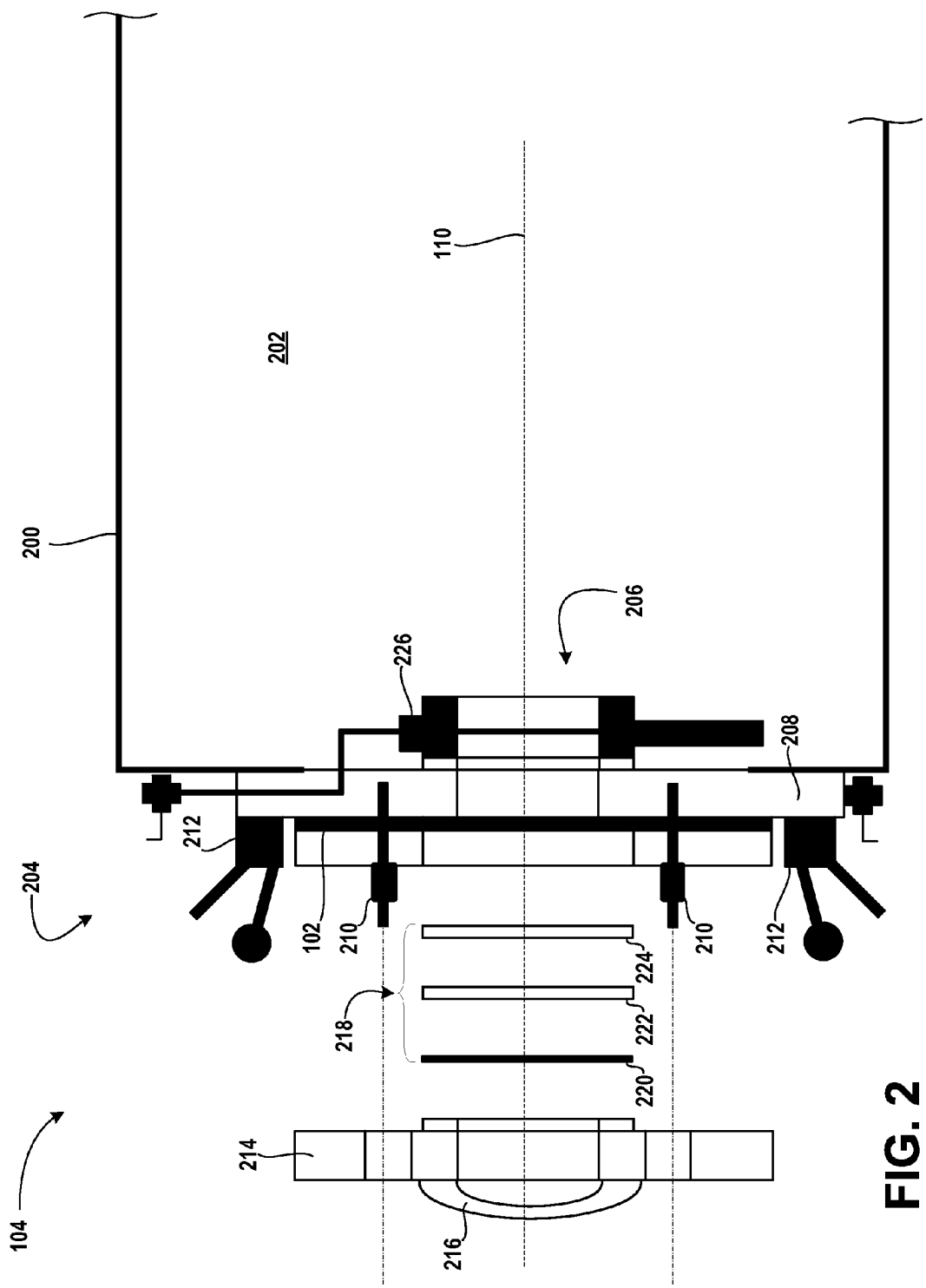
FIG. 2 is a line diagram illustrating aspects of a self-sealing fuel tank test fixture, according to an illustrative embodiment.

Turning now to FIG. 2, additional aspects of the test fixture 104 will be described in detail. As shown in FIG. 2, the test fixture 104 includes a fuel cube 200. The fuel cube 200 provides a structure for storing fuel 202 used for testing the self-sealing properties of the test sample 102. The fuel 202 can include additives for interacting with the self-sealing material, as mentioned above. In some embodiments, additional structures can be located within the fuel cube 200, some embodiments of which will be illustrated and described below with reference to FIG. 3.

As shown in FIG. 2, the test sample 102 can be located at a front side 204 of the test fixture 104. The front side 204 of the test fixture 104 is a side of the test fixture 104 that is exposed to the projectile 106 during testing. As shown, the test sample 102 can be located such that the test sample 102 covers a projectile entry port 206 through which the projectile 106 enters the test fixture 104 while the projectile 106 travels along the projectile path 110 described and illustrated above in FIG. 1A.

According to various implementations, the test sample 102 is attached to a front plate 208 located at the front side 204 of the test fixture 104. The front plate 208 can be secured to the front side 204 of the test fixture 104 with one or more attachment mechanisms. The attachment mechanisms can include, but are not limited to, bolts, adhesives, thermal bonding processes, combinations thereof, and the like. In the illustrated embodiment, the test sample 102 is secured to the front plate 208 with two or more knurled nuts 210, as shown in FIG. 2. The test sample 102 also can be held in place by one or more quick release clamps 212, if desired. The quick release clamps 212 can be operated to allow quick and easy access to the test sample 102 after testing to allow access and/or visual inspection of the test sample 102, if desired. Other attachment mechanisms are possible and are contemplated. As such, the illustrated and described embodiments should be understand as being illustrative and should not be construed as being limiting in any way.

According to various implementations of the concepts and technologies disclosed herein, the quick release clamps 212 engage a face plate 214 that can be held in place by the quick release clamps 212 attached to the front side 204 of the test fixture 104. The face plate 214 is configured to cover the test sample 102 and/or to hold other structures in place over the projectile entry port 206. The face plate 214 can include one or more handles 216 for handling the face plate 214. The front plate 208 also can include external sight gauges that visually give an indication of the amount/height of the fuel inside the fuel cube 200.

According to embodiments of the concepts and technologies disclosed herein, the face plate 214 is used to hold support materials 218 in place in front of the test sample 102. In some implementations, the support materials 218 placed in front of the test sample 102 can, but do not necessarily, include samples formed from materials used in aircraft and/or fuel tank skins. Thus, the support materials 218 can be used to simulate real-world encounters, and therefore real-world testing of the self-sealing materials used to form the test sample 102. Additionally, as is explained herein, the support materials 218 can be chosen to reduce the projectile coring phenomenon described above.

According to some embodiments, the support materials 218 include an aluminum disc, plate, or other aluminum component having any desired shape ("aluminum component") 220. The aluminum component 220 is provided, in some embodiments, by a 0.025 inch thick piece of 7075-T6 aluminum. The 7075-T6 alloy of aluminum is generally known and therefore is not described herein in additional detail. The 0.025 inch thickness is used for the aluminum component 220 to reduce the incidence of projectile coring relative to a 0.125 thickness of aluminum typically used for testing of self-sealing fuel tank materials.

The materials further can include a foam disc, plate, or other foam component having any desired shape ("foam component") 222. In one embodiment, the foam component 222 includes a disc of six pounds per cubic foot foam. As other densities of foam and/or other materials can be used for the foam component 220, it should be understood that this embodiment is illustrative, and should not be construed as being limiting in any way. The materials also can include a backing board disc, plate, or other component having any desired shape ("backing board component") 224. In some implementations the backing board component 224 is a disc of backing board formed from fiberglass or other suitable material(s), though this implementation is illustrative. The aluminum component 220, foam component 222, and the backing board component 224 individually and/or collectively can be used to provide support for the test sample 102. The foam component 222 prevents petalling of the aluminum component 220 from contacting the backing board component 224 and test sample 102. As such, the support materials 218 provide a realistic test of the self-sealing material of the test sample 102, but also provide easy access to the test sample 102 after firing the projectile 106. Furthermore, the use of the support materials as will be described herein can be used to reduce or even eliminate projectile coring.

The test fixture 104 also includes a valve such as a pneumatic knife valve ("knife valve") 226. The knife valve 226 is used to separate the front side 204 of the test fixture 104 from a supply of fuel 202 in the fuel cube 200. It should be understood that the knife valve 226 can be replaced with any suitable valve or other device for providing the functionality described herein with respect to the knife valve 226. As such, the knife valve 226 should be understood as being illustrative of a valve, and should not be construed as being limited in any way.

As will be illustrated and described with reference to FIG. 3, the test fixture 104 can include a fuel plenum that is separated from the fuel cube 200 by the knife valve 226, though the fuel plenum is not illustrated in FIG. 2. In various implementations, the fuel cube 200 holds around one hundred gallons of fuel. As such, if the self-sealing material of the test sample 102 fails, substantial fuel loss can occur. Similarly, there may be no easy way for the tester to access and/or remove the test sample 102, to replace the test sample 102, to visually inspect the test sample 102, and/or to otherwise isolate the front side 204 of the test fixture 104 from the supply of fuel 202.

As such, embodiments of the test fixture 104 include the knife valve 226 to allow isolation of the front side 204 of the test fixture 104 from the supply of fuel 202. After firing the projectile 106 at the test sample 102, and/or upon sealing of the test sample 102, a tester can close the knife valve 226 to seal the test sample 102 from the fuel 202. As such, embodiments of the test fixture 104 allow testers to switch the test sample 102 without losing fuel 202 through the projectile entry port 206.

Figure 3:
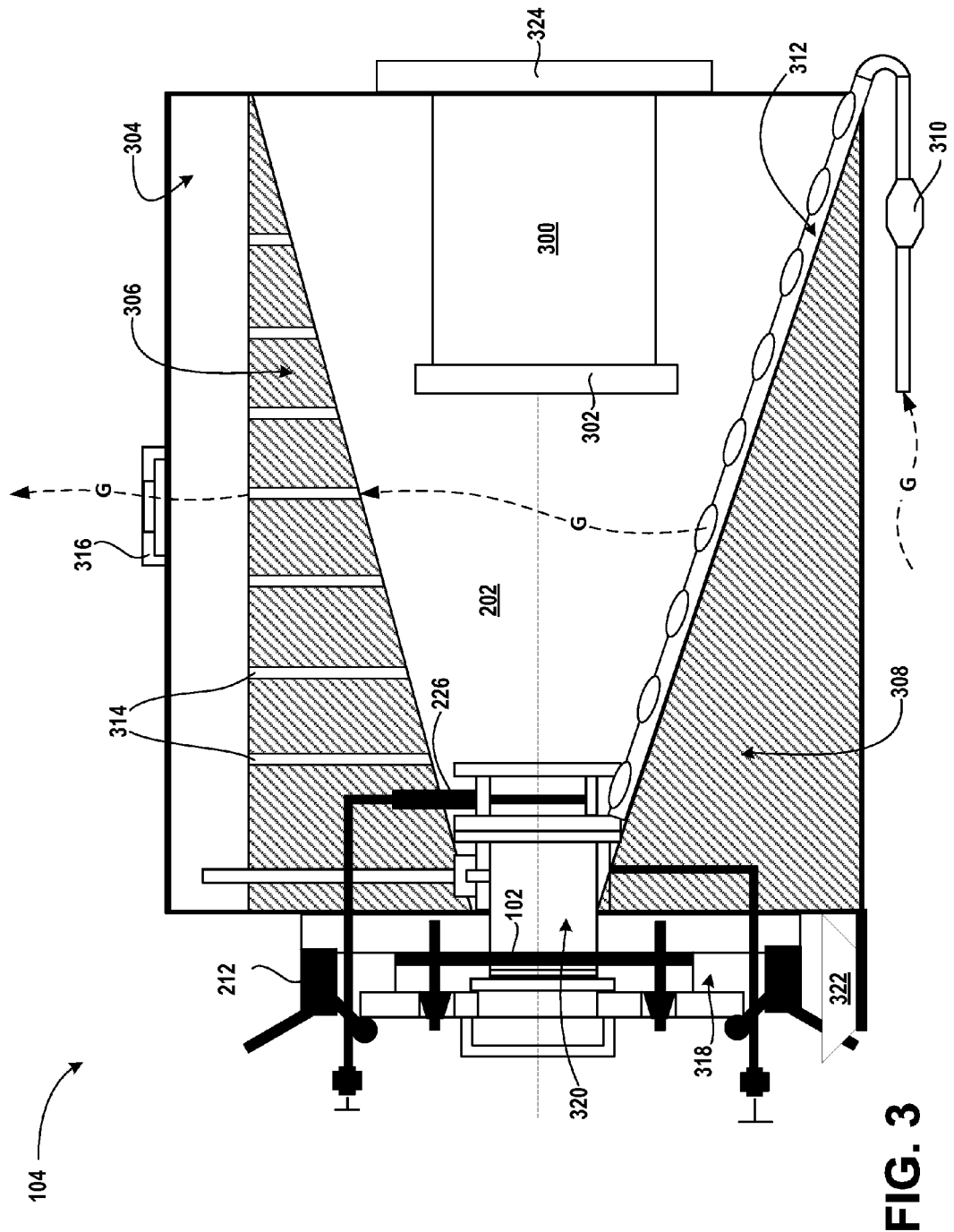
FIG. 3 is a line diagram illustrating additional aspects of a self-sealing fuel tank test fixture, according to another illustrative embodiment.

Turning now to FIG. 3, aspects of another embodiment of the test fixture 104 will be described in detail. It should be understood that the various structures described above with reference to the embodiment illustrated in FIG. 2 can be, but are not necessarily, combined with some or all of the structures described herein with reference to the embodiment illustrated in FIG. 3. The test fixture 104 includes a striker and attenuation plate assembly 300. As shown in FIG. 3, the striker and attenuation plate assembly 300 is located along the projectile path 110.

The striker and attenuation plate assembly 300 includes a strike surface 302 that the projectile 106 strikes after entry into and travel through the test fixture 104. The striker and attenuation plate assembly 300 thus can be used to stop the projectile 106, thereby allowing testing of the test specimen 102 without causing structural damage to the test fixture 104. The striker and attenuation plate assembly 300, among other structures and features described herein, also can be used to reduce the effects of hydrodynamic ram by preventing travel of the projectile 106 and/or a shockwave induced by the projectile 106 to the rear of the test fixture 104.

The test fixture 104 can be filled, partially or completely with fuel 202, as explained above with reference to FIG. 2. In the embodiment illustrated in FIG. 3, the test fixture 104 is partially filled, and therefore includes an ullage 304. It should be understood that the relative size of the ullage 304 and/or a volume, capacity, and/or configuration thereof can be varied. The ullage 304 can be used to provide expansion space for the fuel 202 in the fuel cube 200. As such, embodiments of the concepts and technologies disclosed herein, can provide another method of reducing the effects of hydrodynamic ram by providing expansion space for the fuel 202.

According to various embodiments, the test fixture 104 also includes an upper shock impedance area 306 and a lower shock impedance area 308. The upper shock impedance area 306 and the lower shock impedance area 308 can be used to further reduce the effects of hydrodynamic ram by absorbing the shockwave generated by the projectile 106. According to various implementations, neither, either, or both of the top shock impedance area 306 and/or the lower shock impedance area 308 are formed from foam or another suitable material(s). For example, in some embodiments neither, either, or both of the top shock impedance area 306 and/or the lower shock impedance area 308 can be formed from a polymethacrylimide ("PMI") foam. In some embodiments, the lower shock impedance area 308 is formed from ROHACELL® PMI foam from Evonik Industries. It should be understood that the use of ROHACELL® PMI foam is illustrative, as other foams formed with and without cells can be used as well. The PMI foam used to form the top shock impedance area 306 and/or the lower shock impedance area 308 can have various densities. In one implementation, the top shock impedance area 306 and/or the lower shock impedance area 308 are formed from 2.5 pounds per cubic foot ROHACELL® PMI foam. It should be understood that these embodiments are illustrative, and should not be construed as being limiting in any way.

In some implementations, the test fixture 104 also aerates the fuel 202 in the fuel cube 200 to further reduce the effects of hydrodynamic ram. In particular, the test fixture 104 includes, in various embodiments, a regulator 310 that regulates a flow one or more gas(es) into gas manifold 312 located at or near the bottom of the fuel cube 200 and/or at or near the top of the lower shock impedance area 308. By flowing or injecting gas(es) into the fuel 202, the gas(es) can go into solution in the fuel 202. Thus, embodiments of the test fixture 104 cause the fuel 202 to be impregnated with gas bubbles that absorb shockwaves from the projectile 106. According to some embodiments of the concepts and technologies disclosed herein, the gas injected into the fuel 202 is nitrogen. It should be understood that this embodiment is illustrative, and should not be construed as being limiting in any way. In particular, suitable gases or other fluids other than nitrogen can be used, if desired.

The gas can be injected into the fuel 202 at any desired time. In some embodiments, the gas is injected into the fuel 202 during any desired duration of time leading up to firing the projectile 106 at the test fixture 104. The gas can be injected into the fuel 202 via the regulator 310 and/or the gas manifold 312. When in solution in the fuel 202, the gas can create air spaces that function to further absorb the shockwave induced by the projectile 106. It should be understood that this embodiment is illustrative, and should not be construed as being limiting in any way.

The gas flows through the fuel 202 and through any number of gas escape ports 314 that can be, but are not necessarily, formed in the top shock impedance area 306. The gas can pass through the gas escape ports 314 and into the ullage 304. From the ullage 304, the gas can pass into and/or through a gas escape vent 316 formed in the fuel cube 202 and out of the test fixture 104. It should be understood that this embodiment is illustrative, and should not be construed as being limiting in any way.

In some embodiments, the test fixture 104 includes a drain path 318. The drain path 318 is a path along which fuel 202 leaking through or around the test sample 102 and/or the support materials 218 travels. In some embodiments, the drain path 318 begins at a fuel plenum 320 defined by the test sample 102 and the knife valve 226. It should be understood that this embodiment is illustrative, and should not be construed as being limiting in any way.

The fuel 202 leaking through or around the test sample 102 and/or the support materials 218 can travel along the drain path 318 and into a catch basin 322 that can be located in an appropriate position for catching the fuel 202. As such, the amount of fuel 202 that leaks through or around the test sample 102 and/or the support materials 218 can be measured definitively, thus allowing comparison to other fuels, self-sealing materials used for the test sample 102, fuel additives, materials used for the support materials 218, and the like.

In some embodiments, the test fixture 104 includes an access plate 324. The access plate 324 can be removable, if desired, to allow access into the fuel cube 200 for cleaning, drainage, maintenance, and/or other purposes. The access plate 324 can be attached to the fuel cube 200 using any appropriate attachment mechanism including, but not limited to, screws, nuts, bolts, and the like.

From the above description of the test fixture 104, it can be appreciated that embodiments of the concepts and technologies disclosed herein allow gunfire or other puncture testing of self-sealing materials such as the test sample 102 in a manner that allows easy inspection of the test sample 102 immediately after gunfire or other puncture of the test sample 102. Also, embodiments of the concepts and technologies disclosed herein allow gunfire testing of self-sealing materials such as the test sample 102 in a manner that reduces or eliminates hydrodynamic ram and/or projectile coring often associated with such testing. Still further embodiments of the concepts and technologies disclosed herein allow quantitative analysis of fuel loss resulting from gunfire testing instead of, or in addition to, estimation techniques sometimes used out of necessity in evaluating gunfire or other puncture testing of self-sealing materials.

Figure 4:
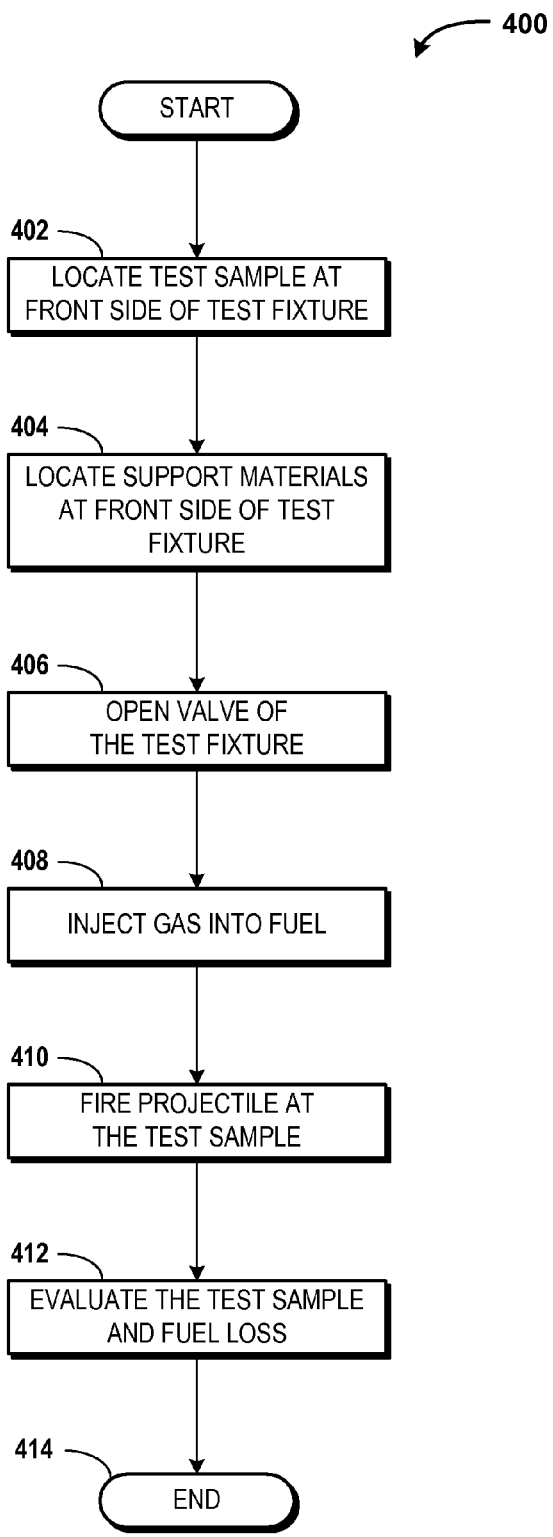
FIG. 4 is a flow diagram illustrating aspects of a method for performing testing of self-sealing fuel tank materials, according to an illustrative embodiment.

Turning now to FIG. 4, aspects of a method 400 for using a self-sealing fuel tank test fixture will be described in detail, according to an illustrative embodiment. It should be understood that the operations of the method 400 disclosed herein are not necessarily presented in any particular order and that performance of some or all of the operations in an alternative order(s) is possible and is contemplated. The operations have been presented in the demonstrated order for ease of description and illustration. Operations may be added, omitted, and/or performed simultaneously, without departing from the scope of the appended claims. It also should be understood that the illustrated method 400 can be ended at any time and need not be performed in their respective entireties.

The method 400 begins at operation 402, wherein a test sample 102 is located at a front side 204 of the test fixture 104. As explained above with reference to FIG. 2, the front side 204 of the test fixture 104 can be, but is not necessarily, a side of the test fixture 104 that faces the firearm 108 or other device that fires the projectile 106 at the test sample 102. The test sample 102 includes, in various implementations, a portion of self-sealing material. In some embodiments, the portion of self-sealing material measures about twelve inches by about twelve inches. It should be understood that this embodiment is illustrative, and should not be construed as being limiting in any way.

From operation 402, the method 400 proceeds to operation 404, wherein the support materials 218 are located at the front side 204 of the test fixture 104. As explained above with reference to FIGS. 2-3, the support materials 218 can be located between the face plate 214 and the test sample 102, and can be held in place by the face plate 214 and/or quick release claims 212. The support materials 218 can be used to reduce petalling of materials adjacent to the test sample 102 and/or to reduce or eliminate projectile coring sometimes associated with testing of self-sealing materials.

From operation 404, the method 400 proceeds to operation 406, wherein the knife valve 226 is opened. It can be appreciated from the description herein that the fuel 202 in the fuel cube 200 can be separated from the test sample 102 before the knife valve 226 is opened, and that after opening the knife valve, the fuel 202 within the fuel cube 200 can move to a position adjacent to the test sample 102. Conversely, although not explicitly illustrated in FIG. 4, closing the knife valve 226 can separate the fuel 202 from the test sample 102, thus allowing removal of the test sample 102 without risking fuel loss and/or without requiring drainage of the fuel 202 from the fuel cube 200. It should be understood that this embodiment is illustrative, and should not be construed as being limiting in any way.

From operation 406, the method 400 proceeds to operation 408, wherein gas is injected into the fuel 202. As explained above, the gas such as nitrogen or other suitable fluids, can be injected into the fuel 202 via the regulator 310 and the gas manifold 312, if desired. Furthermore, as mentioned above, the gas can be used to further reduce the effects of any shockwave(s) induced by movement of the projectile 106 into or through the test sample 102 and/or the fuel 202 within the fuel cube 200.

From operation 408, the method 400 proceeds to operation 410, wherein the projectile 106 is fired at the test sample 102. As noted above, the projectile 106 can be fired from a firearm 108. In some embodiments, the projectile 106 is a .50 caliber bullet fired from a .50 caliber firearm, though this embodiment is illustrative. In other embodiments, the projectile 106 is fired from a rail gun, a pneumatic weapon, and/or another platform, if desired. As such, the embodiment illustrated in FIG. 1A should be understood as being illustrative of one embodiment and should not be construed as being limiting in any way.

From operation 410, the method 400 proceeds to operation 412, wherein the test sample 102, the support materials 218, and/or any fuel loss occurring as a result of the testing are evaluated. As explained with reference to FIG. 2, the face plate 214 can be easily and quickly removed from in front of the test sample 102 by disengaging the quick release clamps 212, thereby allowing visual inspection of the test sample 102. Also, as noted above with reference to FIG. 3, an amount of fuel 202 that leaks around or through the test sample 102 can be measured via collection, and measurement, of the fuel 202 in the drain basin 322. Additionally, a wound in the self-sealing material of the test sample 102 can be examined to determine if the wound has self-sealed, and if so, whether the seal is dry, damp, or wet, thereby indicating if the test sample 102 has successful sealed, partially sealed, or failed, respectively. It should be understood that these embodiments are illustrative, and should not be construed as being limiting in any way. From operation 412, the method 400 proceeds to operation 414 and ends.

Although not illustrated in FIG. 4, it should be understood that the method 400 can be iterated any number of times. In particular, a test sample 102 can be tested a number of times, if desired. Furthermore, the test sample 102 can be replaced, if desired, for alternative or additional testing. It can be appreciated from the description herein, that the knife valve 226 can be closed to switch the test sample 102 and/or for other purposes, if desired. After replacing the test sample 102, or determining that additional testing is to be conducted, the method 400 can return to operation 406 for another iteration of steps 406-412.

Based on the foregoing, it should be appreciated that concepts and technologies for making and using self-sealing fuel tank test fixtures are provided herein. Although the subject matter presented herein has been described in language specific to structural features and methodological acts, it is to be understood that the invention defined in the appended claims is not necessarily limited to the specific features or acts described herein. Rather, the specific features and acts are disclosed as example forms of implementing the claims.

The subject matter described above is provided by way of illustration only and should not be construed as limiting. Various modifications and changes may be made to the subject matter described herein without following the example embodiments and applications illustrated and described, and without departing from the true spirit and scope of the present invention, which is set forth in the following claims.

We claim:

1. A self-sealing fuel tank test fixture comprising:
    a fuel cube configured for storing fuel, the fuel cube comprising a front side configured to support a self-sealing test sample for a puncture test; and
    a valve disposed inside and proximate to the front side of the fuel cube, the valve being selectively configurable from a first position in which the fuel in the fuel cube is separated from the front side and a second position in which the fuel in the fuel cube is allowed to contact the test sample.

2. The test fixture of claim 1, further comprising a face plate located proximate to the front side.

3. The test fixture of claim 2, wherein the face plate is configured to support a supporting material in a location proximate to the test sample.

4. The test fixture of claim 3, wherein the supporting material comprises an aluminum component, a foam component, and a backing board component.

5. The test fixture of claim 1, further comprising a top shock impedance area located within the fuel cube and a bottom shock impedance area located within the fuel cube, each of the top shock impedance area and the bottom shock impedance area being configured to absorb a shockwave created by a projectile traveling into the fuel cube.

6. The test fixture of claim 1, further comprising a striker and attenuation plate assembly located within the fuel cube, the striker and attenuation plate assembly being configured to stop the projectile from exiting the fuel cube.

7. The test fixture of claim 1, further comprising a gas manifold via which gas is distributed into the fuel within the fuel cube.

8. The test fixture of claim 7, wherein the top shock impendence area further comprises at least one gas escape port and a gas escape vent, wherein the gas exits the fuel cube through the at least one gas escape port and the gas escape vent.

9. The test fixture of claim 8, wherein at least one of the top impedance area or the bottom shock impedance area is formed from foam.

10. The test fixture of claim 9, wherein the foam comprises a polymethacrylimide foam having a density of approximately two and a half pounds per cubic foot.

11. A system for testing a test sample of self-sealing material, the system comprising a self-sealing fuel tank test fixture configured to hold the test sample in a position at a front side of the self-sealing fuel tank test fixture for the testing, the self-sealing fuel tank test fixture comprising:
a fuel cube configured for storing fuel,
a face plate located proximate to the front side, the face plate being configure to support at least one supporting material;
at least one shock impedance area configured to absorb a shockwave created by a projectile traveling into the fuel cube, and
a knife valve disposed proximate to the fuel cube, the knife valve being selectively configurable from a first position in which the fuel in the fuel cube is separated from the test sample to a second position in which the fuel in the fuel cube is allowed to contact the test sample.

12. The system of claim 11, wherein the at least one supporting material comprises an aluminum component, a foam component, and a backing board component in position at a location proximate to the test sample.

13. The system of claim 11, wherein the at least one shock impedance area comprises at least one of:
a top shock impedance area located within the fuel cube, the top shock impedance area being configured to absorb the shockwave created by the projectile travelling into the fuel cube;
a bottom shock impedance area located within the fuel cube, the bottom shock impedance area being configured to absorb the shockwave created by the projectile traveling into the fuel cube; or
a striker and attenuation plate assembly located within the fuel cube, the striker and attenuation plate assembly being configured to absorb the shockwave created by the projectile traveling into the fuel cube.

14. The system of claim 13, wherein the self-sealing fuel tank test fixture further comprises a gas manifold via which a gas is distributed into fuel within the fuel cube, and wherein the top shock impendence area further comprises at least one gas escape port and a gas escape vent, wherein the gas exits the fuel cube through the at least one gas escape port and the gas escape vent.

15. The system of claim 11, wherein the device comprises a firearm, and wherein the projectile comprises a bullet fired from the firearm.

16. The system of claim 11, wherein at least one of the top impedance area or the bottom shock impedance area is formed from polymethacrylimide foam having a density of approximately two and a half pounds per cubic foot.

17. A method for using a self-sealing fuel tank test fixture to test a self-sealing test sample, the method comprising:
positioning the test sample at a front side of the self-sealing fuel tank test fixture;
positioning a support material at the front side of the self-sealing fuel tank test fixture;
providing fuel in a fuel cube of the self-sealing fuel tank test fixture wherein the fuel contacts the test sample;
injecting gas into the fuel; and
firing a projectile at the test sample.

18. The method of claim 17, wherein firing the projectile comprises firing a bullet from a firearm.

19. The method of claim 17, wherein injecting the gas comprises flowing the gas into the fuel via a gas manifold disposed proximate to a lower shock impedance area and directing the gas through at least one gas escape port disposed in a top shock impedance area, at least one of top shock impedance area and the bottom shock impedance area being configured to absorb a shockwave created by the projectile when the projectile travels into the fuel cube via a projectile entry port formed in the fuel cube.

20. The method of claim 17, further comprising evaluating at last one of the test sample or a fuel loss observed at the test sample.

* * * * *